US006375990B1

(12) United States Patent
Nemeroff et al.

(10) Patent No.: US 6,375,990 B1
(45) Date of Patent: Apr. 23, 2002

(54) METHOD AND DEVICES FOR TRANSDERMAL DELIVERY OF LITHIUM

(75) Inventors: Charles B. Nemeroff; Clinton D. Kilts, both of Atlanta, GA (US)

(73) Assignee: Emory University, Atlanta, GA (US)

(*) Notice: Subject to any disclaimer, the term of this patent is extended or adjusted under 35 U.S.C. 154(b) by 0 days.

(21) Appl. No.: 09/529,248

(22) PCT Filed: Oct. 9, 1998

(86) PCT No.: PCT/US98/21320

§ 371 Date: May 24, 2000

§ 102(e) Date: May 24, 2000

(87) PCT Pub. No.: WO99/18797

PCT Pub. Date: Apr. 22, 1999

Related U.S. Application Data
(60) Provisional application No. 60/062,148, filed on Oct. 9, 1997.

(51) Int. Cl.[7] .............................................. A61K 33/36
(52) U.S. Cl. ...................................................... 424/667
(58) Field of Search ........................................ 424/667

(56) References Cited

U.S. PATENT DOCUMENTS

| | | | |
|---|---|---|---|
| 4,624,847 A | 11/1986 | Ayer et al. | 424/400 |
| 4,744,787 A | 5/1988 | Phipps et al. | 424/410 |
| 4,747,819 A | 5/1988 | Phipps et al. | 424/491 |
| 4,950,229 A | 8/1990 | Sage, Jr. | 424/492 |
| 5,037,381 A | 8/1991 | Bock et al. | 424/492 |
| 5,057,072 A | 10/1991 | Phipps et al. | 424/493 |
| 5,084,006 A | 1/1992 | Lew et al. | 424/485 |
| 5,131,403 A | 7/1992 | Haynes | 424/485 |
| 5,135,477 A | 8/1992 | Untereker et al. | 424/497 |
| 5,147,297 A | 9/1992 | Myers et al. | 424/497 |
| 5,162,042 A | 11/1992 | Gyory et al. | 424/667 |
| 5,162,043 A | 11/1992 | Lew et al. | 424/666 |
| 5,167,616 A | 12/1992 | Haak et al. | 424/497 |
| 5,203,768 A | 4/1993 | Haak et al. | 424/477 |
| 5,213,568 A | 5/1993 | Lattin et al. | 424/667 |
| 5,223,271 A | 6/1993 | Horrobin | 424/667 |
| 5,246,418 A | 9/1993 | Haynes et al. | 424/492 |
| 5,252,333 A | 10/1993 | Horrobin | 424/497 |
| 5,256,137 A | 10/1993 | Sage, Jr. | 424/497 |
| 5,260,066 A | 11/1993 | Wood et al. | 424/497 |
| 5,264,219 A | 11/1993 | Godbey et al. | 424/486 |
| 5,284,471 A | 2/1994 | Sage, Jr. | 424/666 |
| 5,288,503 A * | 2/1994 | Wood et al. | 424/497 |
| 5,302,172 A | 4/1994 | Sage, Jr. et al. | 424/666 |
| 5,306,235 A | 4/1994 | Haynes | 424/491 |
| 5,310,403 A | 5/1994 | Haynes | 424/492 |
| 5,312,326 A | 5/1994 | Myers et al. | 424/492 |
| 5,314,502 A | 5/1994 | McNichols et al. | 424/497 |
| 5,320,597 A | 6/1994 | Sage, Jr. et al. | 424/497 |
| 5,320,598 A | 6/1994 | Haak et al. | 424/496 |
| 5,326,341 A | 7/1994 | Law et al. | 424/466 |
| 5,334,138 A | 8/1994 | Sage, Jr. et al. | 424/667 |
| D352,113 S | 11/1994 | Ashley | |
| D352,357 S | 11/1994 | Ashley | |
| D352,782 S | 11/1994 | Kirk, III et al. | |
| 5,372,819 A | 12/1994 | Godbey et al. | 424/489 |
| 5,374,242 A | 12/1994 | Haak et al. | 604/20 |
| 5,385,543 A | 1/1995 | Haak et al. | 604/21 |
| 5,387,189 A | 2/1995 | Gory et al. | 424/491 |
| 5,395,310 A | 3/1995 | Untereker et al. | 424/492 |
| 5,405,317 A | 4/1995 | Myers et al. | 424/497 |
| 5,411,737 A | 5/1995 | Hsu et al. | 604/21 |
| 5,415,628 A | 5/1995 | Untereker et al. | 604/21 |
| 5,423,739 A | 6/1995 | Phipps et al. | 424/497 |
| 5,427,585 A | 6/1995 | Bettinger | 424/492 |
| 5,458,569 A | 10/1995 | Kirk, III et al. | 424/492 |
| 5,460,821 A | 10/1995 | Masiz | 424/489 |
| 5,464,387 A | 11/1995 | Haak et al. | 424/489 |
| 5,466,217 A | 11/1995 | Myers et al. | 424/490 |

(List continued on next page.)

FOREIGN PATENT DOCUMENTS

| | | |
|---|---|---|
| EP | 0 289204 B1 | 8/1992 |
| EP | 0 535 530 A1 | 4/1993 |
| EP | 0 586 666 B1 | 5/1997 |
| WO | WO 94/17853 | 8/1994 |
| WO | WO 94/27649 | 12/1994 |
| WO | WO 95/09031 | 4/1995 |
| WO | WO 96/09851 | 4/1996 |
| WO | WO 96/10440 | 4/1996 |
| WO | WO 96/10441 | 4/1996 |
| WO | WO 96/15513 | 5/1996 |
| WO | WO 97/07854 | 3/1997 |
| WO | WO 97/11742 | 4/1997 |
| WO | WO 97/11744 | 4/1997 |
| WO | WO 97/12644 | 4/1997 |
| WO | WO 97/23182 | 7/1997 |
| WO | WO 99/18797 | 4/1999 |

OTHER PUBLICATIONS

Frances, A. et al., *Diagnostic and Statistical Manual of Mental Disorders*, Fourth Edition, American Psychiatric Association (1994).

Haas, et al., "An Excitatory Action of Iontophoretically Administered Lithium on Mammallian Central Neurones," *Br. J,. Pharmac.*, 60:185–195 (1977).

Phipps et al., "Iontophoretic Delivery of Model Inorganic and Drug Ions," *Inl. Of Pharm. Sci.*, 78(5):365–369 (1989).

Phipps, et al., "Transdermal lion Migration," *Advanced Drug Delivery Reviews*, 9:P137–176 (1992).

Prausnitz, et al., "The effects of electric current applied to skin: A review for transdermal drug delivery," *Advanced Drug Delivery Reviews*, 18:395–425 (1996).

Primary Examiner—Dwayne C. Jones
(74) *Attorney, Agent, or Firm*—Bruce D. Gray; Kilpatrick Stockton LLP (57) ABSTRACT

A method and device for treating acute mania or bipolar disorder is disclosed, by transdermal delivery of $Li^+$ at substantially constant rate through the skin via a dermal patch.

36 Claims, 1 Drawing Sheet

U.S. PATENT DOCUMENTS

| | | | |
|---|---|---|---|
| D366,702 S | 1/1996 | Kirk, III et al. | 424/497 |
| 5,494,679 A | 2/1996 | Sage, Jr. et al. | 604/20 |
| 5,496,266 A | 3/1996 | Haak et al. | 604/20 |
| 5,498,235 A | 3/1996 | Flower | 424/466 |
| 5,533,972 A | 7/1996 | Gyory et al. | 424/489 |
| 5,540,669 A | 7/1996 | Sage, Jr. et al. | 424/489 |
| 5,543,098 A | 8/1996 | Myers et al. | 424/497 |
| 5,554,380 A | 9/1996 | Cuca et al. | 424/496 |
| 5,558,633 A | 9/1996 | Phipps et al. | 424/491 |
| 5,573,503 A * | 11/1996 | Untereker et al. | 604/20 |
| 5,582,587 A | 12/1996 | Gyory et al. | 604/21 |
| 5,603,955 A | 2/1997 | Gehrke et al. | 604/22 |
| 5,612,059 A | 3/1997 | Cardinal et al. | 424/489 |
| 5,618,265 A | 4/1997 | Myers et al. | 424/489 |
| 5,626,786 A | 5/1997 | Ebert et al. | 424/497 |
| 5,635,204 A | 6/1997 | Gervirtz et al. | 424/489 |
| 5,645,526 A | 7/1997 | Flower | 604/20 |
| 5,645,854 A | 7/1997 | Masiz | 604/21 |
| 5,647,844 A | 7/1997 | Haak et al. | 424/497 |
| 5,651,979 A | 7/1997 | Ron et al. | 604/21 |
| 5,682,726 A | 11/1997 | Green et al. | 604/21 |
| 5,688,231 A | 11/1997 | Flower | 604/20 |
| 5,688,232 A | 11/1997 | Flower | 604/20 |
| 5,693,024 A | 12/1997 | Flower | 604/22 |
| 5,697,896 A | 12/1997 | McNichols et al. | 424/489 |
| 5,698,220 A | 12/1997 | Cardinal et al. | 424/497 |
| 5,723,145 A | 3/1998 | Shikinami et al. | 424/497 |
| 5,733,577 A | 3/1998 | Myers et al. | 424/496 |
| 5,736,580 A | 4/1998 | Huntington et al. | 424/496 |
| 5,744,155 A | 4/1998 | Friedman et al. | 604/20 |
| 5,770,219 A | 6/1998 | Chiang et al. | 424/496 |

* cited by examiner

METHOD AND DEVICES FOR TRANSDERMAL DELIVERY OF LITHIUM

This application is a 371 of PCT/US98/21320, filed Oct. 9, 1998, which claims priority to U.S. Provisional Application Ser. No. 60/062,148, filed Oct. 9, 1997.

BACKGROUND OF THE INVENTION

As a mood stabilizing agent, lithium has a long history of documented efficacy as well as risk associated with its use. Lithium has the narrowest gap between therapeutic and toxic concentrations of any drug routinely prescribed in psychiatric medicine, and is poorly tolerated in one-third or more of treated patients. The incidence and severity of toxicity associated with its use is related to the plasma concentration of $Li^+$ and its rate of rise following conventional oral routes of dosing. Lithium can be lethal in overdose and there is no specific antidote for $Li^+$ intoxication. The safety and tolerability of $Li^+$ could be dramatically improved by the use of a sustained, controlled $Li^+$ delivery system.

Applicants have discovered a transdermal route of delivery as a suitable means of avoiding oral dosing "peaks" and symptomatic "troughs", of minimizing the need for routine blood concentration monitoring, and of decreasing total daily doses, drug interactions, and dosing frequency. These advantages allow improved patient compliance and quality of life for patients treated with $Li^+$. The well-recognized medical-legal liabilities associated with $Li^+$ treatment are substantially changed, and allow an expanded use of $Li^+$ as an effective drug in the treatment of disabling mood disorders and other psychiatric illnesses.

Lithium is a fixed monovalent cation and the lightest of the alkali metals (group 1a of the Periodic Table of the elements). Of relevance to the design of this device, $Li^+$ has the highest energy of hydration of the alkali metals and, as such, can substitute for $Na^+$ (and to a lesser extent $K^+$) for ion transport by biological systems. Lithium is both electroactive and hydrophilic. Lithium is abundant in some alkali metal-spring waters and has numerous industrial applications. Trace amounts of $Li^+$ are found in human tissues; typical human blood plasma concentrations of $Li^+$ are 17 µg/L.

Lithium has no known physiological effects in man. Unlike other psychotropic drugs, $Li^+$ has no discernible psychotropic effects in normal man. The therapeutic efficacy of lithium in the treatment of acute mania and the prophylactic management of bipolar (manic/depressive) disorder has been consistently demonstrated. Lithium, along with the recent addition of valproic acid (Depakote ®, Trademark of Abbot Laboratories, Inc.), are the only drugs currently approved by the US Food and Drug Administration for the treatment of acute mania. Manic-depressive disorder (bipolar disorder) is a chronic, cycling disease that afflicts approximately 1–1.8% of the population. Manic symptoms include hyperactivity, impaired judgment, insomnia, grandiosity and other delusions. Affected individuals exhibit severe functional impairments evidenced by alienation from family, friends, and coworkers; indebtedness; job loss; divorce; and other problems of living. Lithium salts were introduced into psychiatry in 1949 for the treatment of mania and were accepted for this use in the United States in 1970. Evidence for the efficacy of lithium salts in the treatment of mania and the prevention of recurrent symptoms of manic-depressive illness is now highly impressive. The additional use of lithium coadministration in augmentation strategies has been used as a means of enhancing treatment response to a wide range of psychiatric drugs. Both lithium carbonate and lithium citrate are currently in therapeutic use in the US.

In the nearly 50 years of accumulated clinical experience with $Li^+$ no distinctly improved agent has emerged for the treatment of the morbidity and mortality of bipolar disorder. While it remains the first-line therapy for bipolar disorder, the oral administration of $Li^+$ is predictably associated with a large and diverse array of adverse effects that impact negatively on patient compliance and safety. These events are in turn well related to the pharmacokinetics of orally administered formulations. Symptomatic states related to interdose concentration "troughs" or inadvertent noncompliance further exacerbates noncompliance. Only one-third of patients in a recent community sample were estimated to be compliant. The development of sustained or slow release $Li^+$ preparations represents a direct response to the limitations of oral routes of lithium salt administration. However, the performance of these preparations vary between manufacturers and between batches and they are often used in divided daily dosing strategies similar to nonsustained release preparations. Extremely slow release preparations are furthermore associated with pronounced GI irritation. Available sustained release formulations represent an imperfect solution to the limitations of oral lithium dosing. There is thus a clinical need for an alternative dosing strategy for $Li^+$ that is not met by currently available preparations. The device and methods of the present invention offer a novel strategy of transdermal $Li^+$ delivery to enhance the safety and efficacy of a drug of documented effectiveness and value in psychiatric practice.

The device of the present invention was developed to meet pharmacokinetic inadequacies of the use of conventional oral dosing strategies that limit therapeutic applications of lithium in clinical medicine. Such limitations include acute and long term toxic reactions, the emergence of breakthrough symptoms, poor patient compliance, the necessity of therapeutic drug monitoring and a lack of safety in overdose situations. A transdermal delivery system for lithium according to the present invention is suitable for these purposes.

BRIEF DESCRIPTION OF THE INVENTION

A method of administering $Li^+$ to a patient at substantially constant rate without causing significant pain or tissue damage is disclosed. The method involves the attachment of a dermal patch to the patient, wherein the patch delivers $Li^+$ in response to a current, desirably a direct current, even more desirably a pulsed direct current, presumably by iontophoresis. Also disclosed is a dermal patch for use in the method of the present invention. The method and the patch are suitable for the treatment of acute mania, bipolar (manic/depressive) disorder, and other psychiatric illnesses susceptible to treatment with lithium, and is particularly adaptable to long-term administration and treatment.

The transdermal delivery of lithium to the systemic circulation is based on the application of patch technology incorporating an iontophoretic form of electrically assisted drug delivery. In a particular embodiment of the invention, the device uses direct current (dc), desirably pulsed, anodal iontophoretic lithium delivery, with patch placement typically at a site rich in sweat glands, such as at an axillary site. Controlled lithium delivery is dose adjustable and programmable as a function of the applied current density.

The device and method of the present invention allow the administration of lithium ion to the bloodstream within the therapeutic window without peaks (creating damage of toxicity) and troughs (creating the danger of breakthrough symptoms and decreased patient compliance) experienced with conventional methods of lithium administration. Lithium is controllably delivered across at least the stratum corneum, and possibly other layers of the epidermis, using an unobtrusive device that requires minimal compliance activity on the part of the patient.

DETAILED DESCRIPTION OF THE INVENTION

The present invention relates to a dermal patch for administering lithium to a human patient at substantially constant rate without causing significant pain or tissue damage, which patch comprises:

a source of lithium for iontophoretic delivery;

a support for said lithium source;

a current distribution member for delivering a pulsed direct current sufficient to iontophoretically deliver lithium across a stratum corneum layer of the epidermis of said human, said current distribution member comprising an electrochemically active component in electrical connection with a battery, a voltage pulse generator and a precision resistor.

In one embodiment of the present invention, the electrochemically active component of the dermal patch comprises an Ag/AgCl mesh. This also helps to minimize skin irritation and/or discoloration.

In another embodiment of the dermal patch of the present invention, the source of lithium is LiCl, lithium carbonate, or lithium nitrate, or combination thereof In another embodiment of the dermal patch of the present invention, the support for the lithium source comprises a drug reservoir, a tamper-proof occlusive backing, a conductive gel, and a membrane permeable to $Li^+$ suitable for contact with the skin, and optionally an adhesive. The adhesive is suitable for reversibly attaching said patch to the epidermal layer of the skin of the patient.

In another embodiment of the dermal patch of the present invention, $Li^+$ source is not buffered. This helps to avoid or reduce decreases in transdermal iontophoretic drug flux due to competing ions.

In another embodiment of the dermal patch of the present invention, a detoxification or neutralization effective amount of a complexing agent selected from the group consisting of EDTA, EGTA, and pharmaceutically acceptable salts thereof is included in the patch. This complexing agent is typically included in the occlusive backing, so that it detoxifies or neutralizes the lithium in the event that the backing is damaged or ruptured.

In another embodiment of the dermal patch of the present invention, the patch is substantially free of skin permeability enhancers, including organic solvents, such as ethylene glycol. However, while not necessary, skin permeability enhancers may be used if desired.

Another embodiment of the present invention is dermal patch for administering lithium to a human patient at substantially constant rate without causing significant pain or tissue damage, which patch comprises:

a source of lithium for iontophoretic delivery;

a support for said lithium source;

a current distribution member for delivering a pulsed direct current sufficient to iontophoretically deliver lithium across a stratum corneum layer of the epidermis of said human, said current distribution member comprising an electrochemically active component in electrical connection with a battery, a voltage pulse generator and a precision resistor; and a detoxification or neutralization effective amount of a complexing agent selected from EDTA or EGTA or pharmaceutically acceptable salts thereof, wherein the lithium source is unbuffered; and wherein the patch is substantially free of any skin permeability enhancers.

Another embodiment of the present invention is a method of treating acute mania or bipolar (manic/depressive) disorder with lithium, by providing and maintaining blood $Li^+$ concentrations of between about 0.6 and about 1.4 mEq/L in humans in need thereof, which method comprises the steps of (a) providing a dermal patch for administering lithium to a patient at substantially constant rate;

(b) attaching the patch to the patient's skin;

(c) iontophoretically delivering $Li^+$ from said patch to the patient. This embodiment of the invention can further comprise monitoring the blood $Li^+$ concentrations and adjusting the dose rate if necessary to provide and maintain blood $Li^+$ concentrations of between about 0.6 and about 1.4 mEq/L.

This method can use the dermal patch described above for administering lithium to a patient at substantially constant rate without causing significant pain or tissue damage.

More particularly, the method of this embodiment of the present invention comprises providing and attaching a patch that comprises:

a source of lithium for iontophoretic delivery;

a support for said lithium source;

a current distribution member for delivering a pulsed direct current sufficient to iontophoretically deliver lithium across a stratum corneum layer of the epidermis of said human, said current distribution member comprising an electrochemically active component in electrical connection with a battery, a voltage pulse generator and a precision resistor.

In these embodiments of the method of the present invention:

the electrochemically active component of the patch can comprise an Ag/AgCl mesh, in order to minimize skin irritation and discoloration;

the source of lithium may be LiCl, lithium carbonate, or lithium nitrate, or a combination thereof;

the support for lithium in the patch may comprise a drug reservoir, a tamper-proof occlusive backing, a conductive gel, and a membrane permeable to $Li^+$ suitable for contact with epidermal layer of the skin, and optionally an adhesive to reversibly attach said patch to the epidermal layer of the skin of the patient, the lithium source may be unbuffered, in order to avoid or reduce decreases in transdermal iontophoretic drug flux resulting from competing ions;

a detoxification or neutralization effective amount of a complexing agent selected from the group consisting of EDTA, EGTA, and pharmaceutically acceptable salts thereof can be added, desirably to the occlusive backing; and the $Li^+$ composition may be substantially free of skin permeability enhancers, such as ethylene glycol.

Another embodiment of the present invention relates to a method of treating acute mania or bipolar (manic/depressive) disorder with lithium, by providing and maintaining blood $Li^+$ concentrations of between about 0.6 and about 1.4 mEq/L in humans in need thereof, which method comprises the steps of:

(a) providing a dermal patch for administering lithium to a patient at substantially constant rate without causing significant pain or tissue damage;

(b) attaching the patch to the patient's skin;

(c) iontophoretically delivering $Li^+$ from said patch to the patient;

wherein the dermal patch for administering lithium to a patient at substantially constant rate comprises:

a source of lithium for iontophoretic delivery;

a support for said lithium source;

a current distribution member for delivering a pulsed direct current sufficient to iontophoretically deliver lithium across a stratum corneum layer of the epidermis of said human, said current distribution member comprising an electrochermically active component in electrical connection with a battery, a voltage pulse generator and a precision resistor; and a detoxification or neutralization effective amount of a complexing agent selected from the group consisting of EDTA, EGTA, and pharmaceutically acceptable salts thereof;

wherein the patch lithium source is unbuffered, and wherein the patch is substantially free of skin permeability enhancers.

Another embodiment of the present invention relates to method of treating in humans acute mania or bipolar (manic/depressive) disorder comprising the steps of (a) topically applying to the skin of a patient in need of such treatment a transdermal delivery system comprising a source of lithium, and (b) delivering an effective amount of lithium ion to the patient's bloodstream.

Another embodiment of the present invention relates to a method for administering lithium at a substantially constant rate without causing significant pain or tissue damage to a human patient in need thereof, which method comprises:

(a) providing a source of iontophoretically deliverable lithium; and (b) iontophoretically delivering $Li^+$ to said patient.

This method may further comprise monitoring the blood $Li^+$ concentrations and adjusting the dose rate if necessary to provide and maintain blood $Li^+$ concentrations of between about 0.6 and about 1.4 mEq/L. The source of iontophoretically deliverable lithium used in this method may be a dermal patch. In particular, the dermal patch may comprise a current distribution member capable of delivering current sufficient to iontophoretically deliver $Li^+$ across at least the stratum corneum layer of the human epidermis. This current may be direct current, and more particularly may be pulsed direct current. The current may have a density in the range of from about 50 to about 350 $\mu A/cm^2$, desirably between about 50 and about 200 $\mu A/cm^2$, and when pulsed may have a pulse frequency between about 1 and about 10 kHz, more particularly about 4 kHz. The dermal patch used in this embodiment of the present invention may have an on:off ratio duty cycle between about 1 and about 99%, more particularly about 75%.

Desirably, the method of this embodiment of the invention uses a patch wherein the current distribution member does not cause or reduces skin irritation or discoloration or both. This can be achieved using an Ag/AgCl mesh as the current distribution member.

1. Clinical Parameters of Lithium Therapy in the Treatment of Manic Depression and Related Disorders The probability of attaining a therapeutic response to $Li^+$ is related to the obtainment of blood $Li^+$ concentrations within a "therapeutic window" of 0.6–1.4 mEq/L (determined at steady-state 9–12 hours following the previous nighttime dose). Blood serum concentrations of $Li^+$ less than 0.6 mEq/L are associated with a significantly higher rate of relapse of symptoms of bipolar illness and poorer psychosocial functioning, while concentrations higher than 1.4–1.5 mEq/L are associated with a higher incidence of adverse events. Lithium prophylaxis for the treatment of bipolar disorder is typically initiated with the assumption that treatment will be life-long. The discontinuation of lithium prophylaxis is not only associated with virtual certainty of relapse, but may be associated with subsequent refractoriness of symptoms to $Li^+$. Typical therapeutic doses of lithium salts range from about 300 to about 2,400 mg/day (about 55–440 mg $Li^+$), preferably about 300 to about 1,800 mg/day, and are often administered in two or three divided daily doses. Higher doses are used in the management of acute manic symptoms. Daily doses lower than those used in the treatment of acute mania are often used in prophylactic symptom management and in augmentation strategies. Available oral formulations of lithium salts include syrup and both immediate and slow-release pill forms.

2. Toxicology

The clinical use of $Li^+$ is associated with a very narrow margin of safety. The ratio (therapeutic index) between $Li^+$ concentrations associated with toxic and therapeutic effects only differs by a factor of 2 or 3. Lithium has multiple organ effects including actions on the function of the brain, thyroid, kidney, and heart. Lithium toxicity is related to the maximal plasma concentration ($C_{max}$) and its rate of rise following oral administration. Acute intoxication is characterized by vomiting, profuse diarrhea, coarse tremor, ataxia, coma, and convulsions. Symptoms of milder toxicity that are associated with the absorptive peak of $Li^+$ include nausea, diarrhea, abdominal pain, sedation and fine tremor. Lithium-induced polydipsia and polyuria are common. Serious adverse effects related to $Li^+$ actions on the nervous system include confusion, hyperreflexia, gross tremor, dysarthria, seizures, coma and death. These effects warrant the cautious use of $Li^+$ in the medically ill. Adverse effects of $Li^+$ increase greatly when serum concentrations exceed 1.5 mEq/L. Plasma $Li^+$ concentrations exceeding 3.5 mEq/L are associated with life-threatening intoxication. The low therapeutic index for $Li^+$ and the known relationship between circulating $Li^+$ concentrations and therapeutic and toxic effects necessitates the frequent monitoring of serum or plasma $Li^+$ concentrations. An additional limitation to the use of oral lithium administration is the emergence of "breakthrough" manic symptoms associated with "trough" $Li^+$ concentrations in the later stages of drug elimination.

Drug interactions associated with the concomitant administration of other drugs with $Li^+$ relate largely to alterations in sodium balance.

3. Pharmacokinetics

The pharmacokinetics of lithium salts following their oral administration as their solid or liquid dosage forms is well characterized.

As for the absorption properties of lithium salts, a complete dissociation of the lithium salts into their ions occurs after oral administration. $Li^+$ is readily and nearly completely absorbed from the gastrointestinal tract. For immediate release formulations, the time to maximal plasma $Li^+$ concentration ($T_{max}$) occurs 1–4 hours following an oral dose and attain $C_{max}$ values of about 3–20 mEq/L.

In the distribution of lithium salts, $Li^+$ does not bind to blood proteins. The final volume of distribution ($V_d$) is 0.7–0.9 L/kg and approximates that of total body water.

In the elimination of lithium salts, $Li^+$ is excreted primarily (>90%) through the kidneys and $Li^+$ clearance correlates with renal function. Elimination of $Li^+$ through sweat, saliva, and feces accounts for less than 5% of an oral dose. The half-life of $Li^+$ ranges from 18 to 36 hours. Eighty percent of the filtered load of $Li^+$ is reabsorbed in the renal proximal tubules in tandem with $Na^{30}$.

$Li^+$ is not biotransformed, and is not subject to metabolic conversion.

4. Advantages of Transdermal Lithium Delivery to the Systemic Circulation

The general advantages of transdermal drug delivery relative to oral dosing include controlled drug concentrations in the bloodstream, the avoidance of the gastrointestinal tract and hepatic first-pass metabolism, control of absorption, availability of multiple skin sites to avoid local irritation and toxicity, and improved patient compliance due to simpler dosing regimens. Multiple possible routes of transdermal delivery are also available depending on the size, charge, polarity, and potency of the drug to be delivered. The clinical use of lithium will clearly benefit from controlling $Li^+$ concentrations in the bloodstream, to avoid oral dosing "peaks" and decrease systemic toxicity, GI related side effects, and improve patient compliance. Specific properties of $Li^+$ and of human skin are suitable for an effective mechanism of transdermal delivery of $Li^+$ to the systemic circulation.

5. The Skin as a Barrier to Transdermal Drug Delivery

The human skin is the largest organ of the human body, covering an area of about 2 $m^2$ and composing one-sixth of the total body weight. The skin represents the primary defense against invading microorganisms, chemical and mechanical trauma, and UV irradiation. Skin is also essential for the protection of the internal fluid and electrolyte environment of the body. The skin is also a formidable barrier to the transcutaneous delivery of drugs. Human skin varies in thickness from 0.5 to 6 mm depending on the part of the body that it covers. A dense vascular supply to the skin exists about 0.2 mm below its surface and is involved in essential homeostatic functions such as thermoregulation. Human skin has a pH of 3–4 and thus possesses a net negative charge at physiological pH. The relevant result of this net negative charge is that the skin is permselective, i.e., it allows the transport of positively charged species such as $Li^+$ to proceed with less resistance than that of a negatively charged molecule, due to the Donnan exclusion of co-ions.

The use of human skin as a large permselective surface area in close proximity to the systemic circulation for transdermal $Li^+$ delivery is opposed by the outer layer or epidermis of the skin. The epidermis is an avascular stratified cell layer averaging about 0.1–0.2 mm in thickness. The innermost layer of the skin, the dermis, is vascularized with a high density of capillary loops immediately below the dermal-epidermal junction in the papillary layer. Piercing the roughly parallel dermis and epidermis are appendages such as hair follicles and sweat glands, the density of which varies over the surface of the body.

The actual barrier to the transdermal transport of $Li^+$ (and other drugs) is the stratum corneum, the external layer of the epidermis. Relative to the stratum corneum, the transport of ions in the underlying epidermis and dermis approximate freely diffusable conditions. The stratum corneum has a thickness of only about 10–20 $\mu$m and consists of 15 to 20 layers of densely packed hexagonal, disclike cells (about 1 by 30 $\mu$m, also known as corneocytes) separated by thin multilamellar lipid bilayers that contain cholesterol, free fatty acids, and ceramides. Corneocytes are composed of insoluble alpha-keratin filaments and are 50% water-filled under hydrated circumstances. The lamellar bilayer zones separating the corneocytes are about 50 nm in thickness and possess a small amount of bound water. In combination, the densely packed hexagonal, disclike cells (or corneocytes) "bricks" and bilayer lipid region "mortar" function to hinder the transdermal transport of both lipophilic and hydrophilic substances.

In addition to these structural features, the stratum corneum of the human skin exhibits relevant electrical properties of resistance ($10^4$–$10^6$ ohm $cm^2$) and capacitance (1–50 $nF/cm^2$) that influence skin permeability.

Molecular size of a drug is a major determinant of iontophoretic flux. The charge and molecular size of $Li^+$ and the electrical properties of the stratum corneum facilitate the transdermal iontophoretic flux of $Li^+$ down electric and concentration gradient fields, also aided by electroosmotic flow. Different drugs and distinct forms of transdermal transport utilize one or at best several of the available routes to transdermal delivery. As a drug for transdermal delivery, $Li^+$ is perhaps unique in that it represents a substrate for virtually every available pathway of the intercellular/shunt and transcorneocyte routes of delivery through the epidermis. These properties of $Li^+$ make it suitable for attaining the large iontophoretic flux necessary for therapeutic dosing using the transdermal device.

6. Characteristics of a Transdermal Lithium Delivery Device (the Lithium Patch)

The long history of clinical experience with the oral dosing of lithium salts provides clear guidelines for the desired performance of a transdermal $Li^+$ delivery device. Ineffective, therapeutic and toxic circulating $Li^+$ concentrations have been identified and define the window of desired $Li^+$ delivery. Separate dosing requirements of the use of $Li^+$ in the treatment of acute manic symptoms and the long-term management of bipolar disorder have been defined. Patch-type transdermal drug delivery devices of the present invention incorporate into their design the desired performance features of an iontophoretically-assisted transdermal $Li^+$ patch.

A. Performance

Oral dosing with lithium salts results in the well-recognized "saw-tooth" patterns of blood $Li^+$ concentration-time functions. (See FIG. 1.) Such patterns are characterized by marked inter- and intra-individual variability in $T_{max}$ and $C_{max}$, which are pharmacokinetic parameters related to the incidence and magnitude of adverse drug effects. The transdermal iontophoresis of $Li^+$ allows the controlled delivery of a sustained $Li^+$ concentration in the systemic circulation. The resulting decrease in intra and inter-subject variability of $Li^+$ pharmacokinetics decreases systemic toxicity, and minimizes the need for therapeutic drug monitoring with associated venipuncture. The pharmacodynamic outcome of the clinical use of the transdermal $Li^+$ patch is significantly smaller daily doses compared to oral dosing of $Li^+$.

The transdermal $Li^+$ patch allows a controlled delivery of 40 to 240 mg $Li^+$/day to the systemic circulation. Dosage is selectable in approximately 20 mg increments based on the applied current. A range of applied current densities of about 50 to about 350 $\mu$A/cm$^2$ provides the iontophoretic driving force. Each patch would have a performance lifetime of 33 to 200 hours, depending on the desired delivery rate.

It is preferable to have a battery source with a lifetime slightly longer than the performance lifetime, to minimize any confusion over the suitability and the feasibility reapplying the patch to the patient.

B. Patch Components and Their Schematic Organization

The components of one embodiment of the transdermal Li$^+$ patch of the invention include the electrode, battery (constant voltage supply), drug reservoir, adhesive, Li$^+$ permeable membrane, conductive gel, and tamper-proof occlusive backing containing a Li$^+$ complexing agent. The precise nature of adhesive, conductive gel, and occlusive backing are not critical to the present invention, provided that they are suitable materials known in the art for transdermal patches and for iontophoretic delivery systems. For example, the adhesive may be any pressure-sensitive, biomedical adhesive suitable for adhering to skin. The occlusive backing may be any suitable material for continuing a lithium salt solution in a "tamper-proof" manner, and may be, e.g., a plastic material. The conductive gel and porous membrane may be any suitable gel or membrane for use in iontophoresis.

Figure 1:
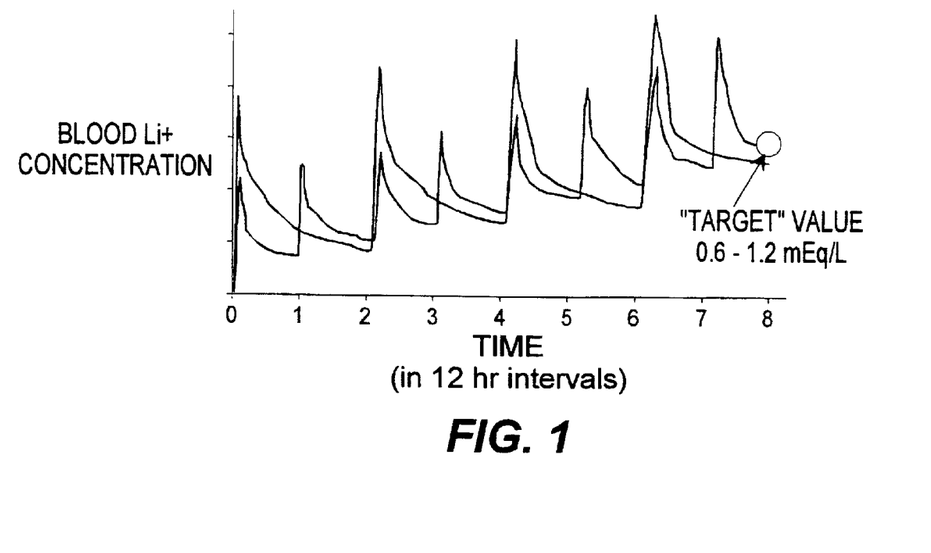
FIG. 1 is a graph setting forth a typical profile of blood $Li^+$ concentration in patients using conventional oral dosing, and illustrates the highly variable concentration that is the source of much of the known toxicity in patients.

In one embodiment of the patch of the present invention, there is a source of lithium to be iontophoretically delivered, comprising LiCl, lithium carbonate, or lithium nitrate, or combination thereof. A support 1 according to FIG. 2 comprises a drug reservoir 2, an occlusive backing 3, preferably a tamper-proof occlusive backing, a conductive gel 4, a membrane 5 permeable to Li$^+$ to contact the skin, and, optionally, adhesive 6 to attach the patch to the skin of the patient. FIG. 1 shows the drug reservoir situated opposite the electrochemically active component from the skin, however it will be recognized that the reservoir may be on the "skin side" of the electrochemically active component, e.g. between the electrochemically active component and the conductive gel or permeable membrane.

Figure 2:
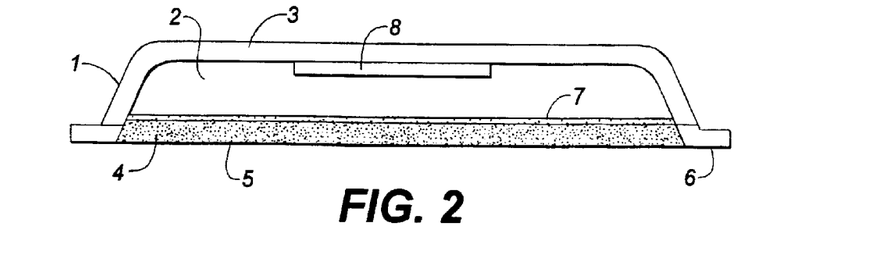
FIG. 2 schematically illustrates one embodiment of the dermal patch of the present invention, in cross section.

A current distribution member in the patch comprises an electrochemically active component 7, and a battery 8. The electrochemically active component 7 comprises silver or platinum in a variety of configurations, but in one embodiment is preferably a Ag/AgCl mesh. The battery 8 is connected to the electrochemically active component typically by a voltage pulse generator and a resistor (not shown).

The drug reservoir has a total volume of between about 5 ml and about 30 ml, preferably about 10 ml. The reservoir contains an unbuffered electroneutral aqueous solution of LiCl, lithium carbonate, or lithium nitrate, preferably LiCl. An initial reservoir concentration of 5 M LiCl is well within the solubility limits (i.e., 595 mg/ml) of LiCl, provides a concentration gradient field, and permits a multiday lifetime for a patch. As a fixed cation, the oxidation state (i.e.,+1) of Li$^+$ is independent of solution pH. Therefore, the addition of buffering agents to maximize drug charge state by controlling solution pH is not necessary, thus avoiding the decrease in transdermal iontophoretic drug flux by competing ions contributed by the buffering agent and maximizing the transport number for Li$^+$.

The electrode to be used for anodal iontophoresis comprises silver or platinum, preferably as Ag/AgCl electrode mesh. The selection of this anode material is based on the lack of pH change of the contents of the drug reservoir by electrolysis during iontophoresis. Localized skin irritation and discoloration are minimized and Li$^+$ delivery is optimized due to the lack of formation of more iontophoretically mobile hydronium ions.

The pulsed dc electrical field representing the iontophoretic driving force for Li$^+$ delivery is generated by a battery, voltage pulse generator and precision resistor. The battery represents typically a constant source of between about 0.25 V and about 10.0 V, preferably between about 0.5 V and about 2.5 V, most preferably about 1 V.

A constant voltage permits variation in the applied current with the changing resistance of the skin. The selection of pulsed rather than continuous dc minimizes skin irritation, and maximizes iontophoretic flux during lengthy current application. The disadvantage of continuous dc for transdermal drug iontophoresis is skin polarization and related skin irritation and reduced drug flux with long durations of current application. Buildup of this polarizable current can be reduced by the use of pulsed dc. To minimize the pulse current density in obtaining the desired time-average applied currents while allowing skin depolarization between pulses, the typical parameters needed are a pulse frequency of between about 1 and about 10 kHz, preferably about 4 kHz, and an on:off ratio duty cycle of between about 1 to about 99%, preferably about 75%.

The transdermal Li$^+$ patch has a surface area of between about 15 cm$^2$ and about 40 cm$^2$, preferably about 25 cm$^2$, with a thickness of between about 15 mm and about 18 mm. The proposed configuration of patch components is viewed in cross section in FIG. 2.

The elements described above can be used in connection with a cathode electrically connected to the current source via a circuit. For example, a separate cathode patch can be applied to the skin and its electrode connected to the current source via an electrically conductive wire or lead through the occlusive backing.

Figure 3:
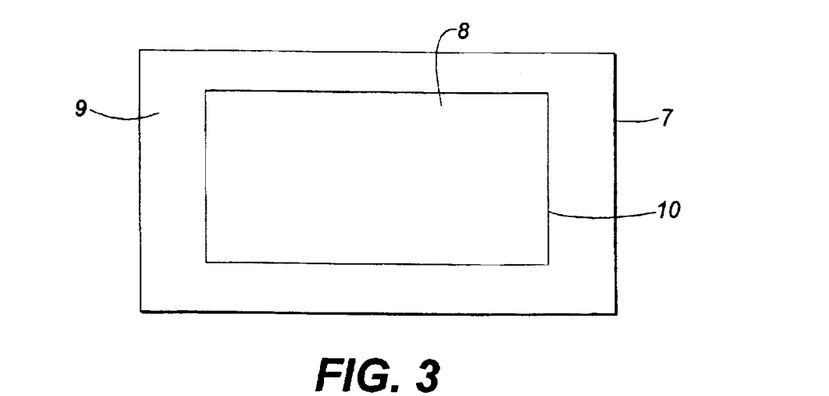
FIG. 3 is a plan view of one embodiment of the present invention showing the arrangement of the current distribution member.

Alternatively, the cathode may form an integral part of the dermal patch, e.g. as an annular ring of Ag/AgCl separated from and surrounding the anode, and connected to the current source via conductive wire disposed in the occlusive backing. Such an arrangement is shown by FIG. 3, which shows electrochemically active component 7 to comprise an anode 8 as the inner portion, a cathode 9 as the outer portion, and optionally an insulating material 10, disposed between the anode and the cathode. The cathode material may be any material suitable for an Iontophoretic cathode, but is desirably Ag/AgCl. Any suitable insulating material may be used as insulating material 10. It will be understood that the electrochemically active component 7 may also be arranged with the cathode in the center and the anode surrounding it, so that in FIG. 3, the cathode would be represented by numeral 8 and the anode by numeral 9. It will also be understood that other shapes than rectangular may be used for the anode and cathode, including, for example, circular or ellipsoid shapes. It will also be understood that the various electrodes may be located in different layers of the dermal patch. For example, the cathode may be located in a layer closer to the skin than is the anode, e.g., on the skin side of the conductive gel or of the porous membrane. In such an arrangement, an insulating material 10 may be largely unnecessary.

While not wishing to be bound by any theory, it is believed that the Ag/AgCl anode is sacrificial, i.e. at least the metallic silver components dissolve into the reservoir as silver ion. This silver ion reacts with the anionic counterion of the lithium salt in the reservoir, typically chloride ion, to form insoluble silver chloride. The decrease in chloride ions promotes diffusion of the Li$^+$ cations through the openings in the anode mesh and into the conductive gel, where the electric field imposed by the anode provides the driving force for moving these cations across the stratum corneum and, desirably, into the sweat glands. The constant migration of lithium cations out of the conductive gel, through the porous membrane, and into the skin creates a concentration gradient across the anode sufficient to overcome any electrostatic force exerted on the lithium cations by any portions of the electrostatic field that might tend to force them back into the reservoir and away from the anode. The result is that the lithium cations move out of the reservoir and across the anode by diffusion resulting from the concentration gradient across the anode, and are then propelled away from the anode and through the conductive gel, porous membrane, and epidermis by the electrostatic force exerted by the electric field in the vicinity of the anode.

C. Dosing features

The steady state iontophoretic flux of Li$^+$ ($J_{Li}$) is proportional to the applied current density, $I_T$:

$$J_{Li} = I_T t_{Li}/z_{Li} F$$

where $t_{Li}$ refers to the transport number for Li$^+$, $Z_{Li}$ the charge (+1) of the lithium ion, and F the Faraday constant.

A linear increase in the iontophoretic delivery rate of Li$^+$, and of numerous other inorganic and organic compounds, with increases in the applied current density has been demonstrated. This linear relationship allows a precise control of transdermal iontophoretic Li$^+$ flux and permits the preprogrammed delivery of Li$^+$ from a skin patch.

D. Recommended use

One preferred transdermal Li$^+$ patch is intended for replacement on a daily basis. This recommended schedule of daily replacement is intended to facilitate a routine and more reliable patient use, and to minimize local skin reactions. A much longer functional life of the patch increases the likelihood of inconsistent patch replacement, a result that should be avoided in the symptom management of the patients with the device.

A major route of transdermal Li$^+$ flux occurs via an appendageal pathway consisting of iontophoretic delivery through the sweat gland duct and subsequent intradermal transport by substitution for sodium transport in the duct. Therefore, the sweat gland-rich axillary region (i.e., >200/cm$^2$) represents a recommended site of patch placement. Use of this inconspicuous underarm site should also promote patch use.

For monitoring of Li$^+$ concentration, initial patch application is followed within about 48 to about 72 hours by the collection of a venous blood sample to determine the blood Li$^+$ concentration associated with the initial applied current, and to adjust the current density if necessary. A second blood Li$^+$ concentration determination is performed about at least 2 weeks later to assure reliable patch performance and patient compliance, and thereafter repeated as desired. The transdermal Li$^+$ patch is not intended to substitute for the clinical monitoring of symptoms and drug side effects.

E. Safety and Tolerability

Lithium can be lethal in overdose and lithium has a long history of involvement in suicide. The patch improves greatly the risks associated with intentional or inadvertent Li$^+$ overdose by decreasing the accessibility of Li$^+$. A durable occlusive backing hinders access to the drug reservoir. Further, it is preferred to include a Li$^+$ complexing agent sandwiched between the backing and drug reservoir, so that the agent is released into the reservoir if the patch is damaged.

The patch is suitable for daily long term use in the management of acute mania and prophylaxis of bipolar disorder. It is also suitable for augmenting the effects of other psychiatric drugs. Patch tolerability in long term use is addressed by the use of biocompatible components for the electrode, conductive gel and adhesive. The use of a conductive gel prevents skin "breakdown" due to direct electrode contact with the skin. Skin irritation or damage is also minimized by the daily rotation of patch placement to the other and opposite axillary site. Unlike many other available transdermal drug delivery devices, the patch does not use, and is substantially free of, skin irritating organic solvents as permeability enhancers including, e.g., ethylene glycol.

An important limitation to long term tolerability of the patch is localized sensation, pain or muscle stimulation due to the skin application of an electrical field. The applied current density and frequency to be used as the iontophoretic driving force for transdermal Li$^+$ delivery are selected to remain below accepted threshold values for muscle stimulation, sensation or pain. The stimulation of nerves by electric fields that exceed a perception threshold can result in painless sensations described most often as tingling or itching; pain thresholds are generally 3–215 times greater than perception thresholds. A current density of about 500 $\mu$A/cm$^2$ is the approximate limit for tolerated sensation. See, e.g. Prausnitz, M. R., Advance Drug Delivery Reviews 18, 395 (1996). The largest time-average current density proposed for the management of acute mania by transdermal Li$^+$ delivery represents a density that is 70% of this limit. Furthermore, the impact of localized sensations related to drug iontophoresis on the tolerability of the patch should be lessened by an increase in perception thresholds with time, and the use of pulsed dc iontophoresis. The lower current densities (<200 $\mu$A/cm$^2$) are suitable for the long term prophylaxis and lithium augmentation strategies of the present invention.

F. Particular Embodiments Relating to Safety and Tolerability.

In typical embodiments of the patch technology of the present invention, no buffering agents for Li$^+$ are needed, since it is not necessary to avoid decreases in transdermal iontophoretic drug flux by competing ions. Another alternative feature of the present invention is the incorporation of complexing agents, such as EDTA or EGTA, for detoxification or neutralization. Still another embodiment is a patch without skin permeability enhancers. The choice of the appropriate organic solvent for such a patch without skin permeability enhancers is within the skill of the art.

G. Cost

Lithium is the least expensive drug used in psychiatric practice. Cost savings can also occur if interchangeable drug reservoirs are used with a battery/current source/backing system to lower the total cost of daily patch replacement. Also the use of continuous as opposed to pulsed dc as the iontophoretic driving force for Li$^+$ delivery simplifies patch design and reduces cost.

7. Mental Disorders Suitable for Treatment with Patch Technology

The typical mental disorders suitable for treatment with patch technology of the present invention include acute mania and bipolar (manic/depressive) disorder, as defined in Frances, A. et al. (Eds.) Diagnostic and Statistical Manual of Mental Disorders Fourth Edition American Psychiatric Association 1994. Some of the significant characteristics of the technology of the present invention include better control of drug delivery and of patient compliance, features making the technology suitable for expanded use of lithium in the treatment of disabling mood disorders and other psychiatric illnesses.

EXAMPLE 1

Sherry F. is a 42 year old female with a long history of manic-depressive illness. Her mood swings are extreme and when manic she becomes paranoid, hyperactive and engages in a number of activities that are dangerous to her, including spending sprees, speeding while driving and sexual promiscuity. Although she responds well to treatment with lithium, she is unfortunately unable to tolerate the side effects of either the generic immediate release form of lithium carbonate or the slow release lithium preparations. She experiences severe gastrointestinal upset, nausea and diarrhea when her lithium dose administered orally exceeds 900 mg per day. However, she requires 1500–1800 mg per day to control her symptoms. Because she is unable to tolerate the doses of lithium required to maintain her symptoms, she has been treated with a variety of other medications, including carbamazepine, atypical antipsychotics and valproic acid, all with serious drawbacks in terms of side effects. The application of the transdermal patch of the present invention is suitable to obtain sufficient lithium plasma concentrations without the GI upset.

EXAMPLE 2

Roger S. is a 20 year old man who was institutionalized at a center within a state hospital system for children and adults who are developmentally disabled. Because of trauma associated with birth and associated hypoxia, Roger S. suffered considerable brain damage and, although physically healthy, he suffers from an impulse control disorder characterized by self injury and injury to others. For that reason he has been hospitalized for the last 12 years. He is unwilling to cooperate with taking oral medications and, although lithium has been shown to stabilize his mood and markedly reduce his outbursts, he is unwilling to cooperate with nursing staff to take it. The transdermal patch according to the present invention applied once or twice a week is suitable for treating this patient.

EXAMPLE 3

Peggy R. is a 37 year old female with a long history of intractable and severe depression. She has failed a treatment with a variety of standard antidepressants. Three suicide attempts are known. Lithium converts antidepressant non-responders to responders in approximately 50% of patients who do not respond to antidepressant monotherapy. Application of the transdermal patch of the present invention is suitable to maintain her current antidepressant regimen, minimize the side effects of lithium and to improve her treatment response to the antidepressant.

EXAMPLE 4

Patty G. is an 11 year old girl with a two year history of bipolar disorder in childhood. She has marked temper tantrums, irritability, violent outbursts and wild mood swings. Although she has responded to treatment with lithium, she is unable to comply with orally ingesting lithium tablets three times per day. Application of the transdermal patch of the present invention is suitable for providing substantially constant levels of lithium with minimal side effects.

While the foregoing specification teaches the principles of the present invention, with examples provided for the purpose of illustration, it will be understood that the practice of the invention encompasses all of the usual variations, adaptations, or modifications, as come within the scope of the following claims and its equivalents.

What is claimed is:

1. A method for administering lithium at a substantially constant rate without causing significant pain or tissue damage to a human patient in need thereof, which method comprises:
   (a) providing a source of iontophoretically deliverable lithium; and
   (b) iontophoretically delivering $Li^+$ to said patient.

2. The method of claim 1, further comprising monitoring the blood $Li^+$ concentrations and adjusting the dose rate if necessary to provide and maintain blood $Li^+$ concentrations of between about 0.6 and about 1.4 mEq/L.

3. The method of claim 1, wherein the source of iontophoretically deliverable lithium is a dermal patch.

4. The method of claim 3, wherein the dermal patch comprises a current distribution member capable of delivering current sufficient to iontophoretically deliver $Li^+$ across a stratum corneum of an epidermis of said human.

5. The method of claim 4, wherein said current is direct current.

6. The method of claim 5, wherein said direct current is pulsed direct current.

7. The method of claim 4, wherein said current is provided at a density in the range of from about 50 to about 350 $\mu A/cm^2$.

8. The method of claim 7, wherein the current density is between about 50 and about 200 $\mu A/cm^2$.

9. The method of claim 6, wherein the pulsed direct current has a pulse frequency between about 1 and about 10 kHz.

10. The method of claim 9, wherein the pulse frequency is about 4 kHz.

11. The method of claim 9, wherein patch has an on:off ratio duty cycle between about 1 and about 99%.

12. The method of claim 11, wherein the on:off ratio duty cycle is about 75%.

13. The method of claim 4, wherein the current distribution member does not cause or reduces skin irritation or discoloration or both.

14. The method of claim 13, wherein the current distribution member is an Ag/AgCl mesh.

15. A method of treating in humans acute mania or bipolar (manic/depressive) disorder comprising the steps of
   (a) topically applying to the skin of a patient in need of such treatment a transdermal delivery system comprising a source of lithium, and
   (b) delivering an effective amount of lithium ion to the patient's bloodstream.

16. A dermal patch for administering lithium to a human patient at substantially constant rate without causing significant pain or tissue damage, which patch comprises:
   a source of lithium for iontophoretic delivery;
   a support for said lithium source;
   a current distribution member for delivering a pulsed direct current sufficient to iontophoretically deliver lithium across a stratum corneum layer of the epidermis of said human, said current distribution member comprising an electrochemically active component in electrical connection with a battery, a voltage pulse generator and a precision resistor; and
   a detoxification or neutralization effective amount of a complexing agent selected from EDTA or EGTA or pharmaceutically acceptable salts thereof, wherein the lithium source is unbuffered; and
   wherein the patch is substantially free of any skin permeability enhancers.

17. A method of treating acute mania or bipolar (manic/depressive) disorder with lithium, by providing and maintaining blood $Li^+$ concentrations of between about 0.6 and about 1.4 mEq/L in humans in need thereof, which method comprises the steps of
(a) providing a dermal patch for administering lithium to a patient at substantially constant rate;
(b) attaching the patch to the patient's skin;
(c) iontophoretically delivering $Li^+$ from said patch to the patient.

18. The method of claim 17, further comprising monitoring the blood $Li^+$ concentrations and adjusting the dose rate if necessary to provide and maintain blood $Li^+$ concentrations of between about 0.6 and about 1.4 mEq/L.

19. The method of claim 17, wherein the dermal patch comprises:
a source of lithium for iontophoretic delivery;
a support for said lithium source;
a current distribution member for delivering a pulsed direct current sufficient to iontophoretically deliver lithium across a stratum corneum layer of the epidermis of said human, said current distribution member comprising an electrochemically active component in electrical connection with a battery, a voltage pulse generator and a precision resistor.

20. The method of claim 19, wherein the electrochemically active component of the patch comprises an Ag/AgCl mesh.

21. The method of claim 19, wherein the source of lithium is LiCl, lithium carbonate, or lithium nitrate, or combination thereof.

22. The method of claim 19, wherein the support for lithium in the patch comprises a drug reservoir, a tamper-proof occlusive backing, a conductive gel, and a membrane permeable to $Li^+$ suitable for contact with the epidermal layer of the skin.

23. The method of claim 22, wherein the support further comprises an adhesive.

24. The method of claim 17, wherein the lithium source is unbuffered.

25. The method of claim 17 further comprising detoxification or neutralization effective amount of a complexing agent selected from the group consisting of EDTA, EGTA, and pharmaceutically acceptable salts thereof.

26. The method of claim 17, wherein the patch is substantially free of skin permeability enhancers.

27. A method of treating acute mania or bipolar (manic/depressive) disorder with lithium, by providing and maintaining blood $Li^+$ concentrations of between about 0.6 and about 1.4 mEq/L in humans in need thereof, which method comprises the steps of:
(a) providing a dermal patch for administering lithium to a patient at substantially constant rate without causing significant pain or tissue damage;
(b) attaching the patch to the patient's skin;
(c) iontophoretically delivering $Li^+$ from said patch to the patient;
wherein the dermal patch for administering lithium to a patient at substantially constant rate comprises:
a source of lithium for iontophoretic delivery;
a support for said lithium source;
a current distribution member for delivering a pulsed direct current sufficient to iontophoretically deliver lithium across a stratum corneum layer of the epidermis of said human, said current distribution member comprising an electrochemically active component in electrical connection with a battery, a voltage pulse generator and a precision resistor; and
a detoxification or neutralization effective amount of a complexing agent selected from the group consisting of EDTA, EGTA, and pharmaceutically acceptable salts thereof;
wherein the patch lithium source is unbuffered, and
wherein the patch is substantially free of skin permeability enhancers.

28. A dermal patch for administering lithium to a human patient at substantially constant rate without causing significant pain or tissue damage, which patch comprises:
a source of lithium for iontophoretic delivery;
a support for said lithium source;
a current distribution member for delivering a pulsed direct current sufficient to iontophoretically deliver lithium across a stratum corneum layer of the epidermis of said human, said current distribution member comprising an electrochemically active component in electrical connection with a battery, a voltage pulse generator and a precision resistor.

29. The dermal patch of claim 28, wherein the electrochemically active component comprises an Ag/AgCl mesh.

30. The dermal patch of claim 28, wherein the source of lithium is LiCl, lithium carbonate, or lithium nitrate, or combination thereof.

31. The dermal patch of claim 28, wherein the support for said lithium source comprises a drug reservoir, a tamper-proof occlusive backing, a conductive gel, and a membrane permeable to $Li^+$ suitable for contact with the epidermal layer of the skin.

32. The dermal patch of claim 31, further comprising an adhesive.

33. The dermal patch of claim 28, wherein the lithium source is unbuffered.

34. The dermal patch of claim 31, further comprising a detoxification or neutralization effective amount of a complexing agent selected from the group consisting of EDTA or EGTA or pharmaceutically acceptable salts thereof.

35. The dermal patch of claim 28, wherein the patch is substantially free of skin permeability enhancers.

36. The dermal patch of claim 28, wherein the patch is substantially free of ethylene glycol.

* * * * *